US012214223B2

United States Patent
Ashe et al.

(10) Patent No.: US 12,214,223 B2
(45) Date of Patent: Feb. 4, 2025

(54) NONINVASIVE TISSUE DISPLACEMENT CONTROL AND MONITORING FOR NEUROMODULATION

(71) Applicant: GE Precision Healthcare LLC, Wauwatosa, WI (US)

(72) Inventors: Jeffrey Michael Ashe, Gloversville, NY (US); Christopher Michael Puleo, Niskayuna, NY (US); Victoria Eugenia Cotero, Troy, NY (US); Ying Fan, Schenectady, NY (US); Kirk Dennis Wallace, Schenectady, NY (US); John Frederick Graf, Ballston Lake, NY (US)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/189,011

(22) Filed: Mar. 23, 2023

(65) Prior Publication Data
US 2023/0226380 A1    Jul. 20, 2023

Related U.S. Application Data

(63) Continuation of application No. 16/750,932, filed on Jan. 23, 2020, now Pat. No. 11,633,630.

(51) Int. Cl.
*A61N 7/00* (2006.01)
*A61B 8/00* (2006.01)
*A61B 8/08* (2006.01)

(52) U.S. Cl.
CPC .............. *A61N 7/00* (2013.01); *A61B 8/485* (2013.01); *A61N 2007/0026* (2013.01); *A61N 2007/0082* (2013.01)

(58) Field of Classification Search
CPC .............. A61N 7/00; A61N 2007/0026; A61N 2007/0082; A61B 8/485
See application file for complete search history.

(56) References Cited

U.S. PATENT DOCUMENTS

| | | | |
|---|---|---|---|
| 8,992,426 B2 | 3/2015 | Fan et al. | |
| 9,119,951 B2 | 9/2015 | Gertner et al. | |
| 9,533,148 B2 | 1/2017 | Carcieri | |
| 11,253,732 B2* | 2/2022 | Mayer | G16H 40/63 |
| 2007/0043401 A1 | 2/2007 | John | |
| 2008/0033297 A1 | 2/2008 | Sliwa | |

(Continued)

FOREIGN PATENT DOCUMENTS

| | | |
|---|---|---|
| JP | 2004520870 A | 7/2004 |
| WO | 2013152035 A1 | 10/2013 |

(Continued)

OTHER PUBLICATIONS

Cotero V, Fan Y, Tsaava T, Kressel AM, Hancu I, Coleman TR, Zanos S, Tracey KJ, Chavan SS, Puleo C, Noninvasive sub-organ ultrasound stimulation for targeted neuromodulation. 2019JAN01; 10(1): Article 5337 [12pg.] Available from: https://academicworks.medicine.hofstra.edu/articles/5337. (Year: 2019).

(Continued)

*Primary Examiner* — Sean A Frith
(74) *Attorney, Agent, or Firm* — Fletcher Yoder, P.C.

(57) ABSTRACT

The subject matter of the present disclosure generally relates to techniques for neuromodulation that include applying energy (e.g., ultrasound energy) into an internal tissue to cause tissue displacement and identifying that the tissue displacement has occurred. In one embodiment, the presence of tissue displacement is associated with a desired therapeutic or physiological outcome, such as a change in a molecule of interest.

20 Claims, 17 Drawing Sheets

(56) References Cited

U.S. PATENT DOCUMENTS

| | | | | |
|---|---|---|---|---|
| 2010/0016721 A1* | 1/2010 | Kanai | ................. | G01S 15/8909 |
| | | | | 600/443 |
| 2010/0280373 A1* | 11/2010 | Fan | ..................... | A61B 8/0833 |
| | | | | 600/439 |
| 2013/0296743 A1 | 11/2013 | Lee et al. | | |
| 2015/0359508 A1 | 12/2015 | Littrup et al. | | |
| 2017/0348049 A1* | 12/2017 | Vrba | .................. | A61B 18/1492 |
| 2019/0069949 A1* | 3/2019 | Vrba | ..................... | A61B 18/16 |

FOREIGN PATENT DOCUMENTS

| | | | |
|---|---|---|---|
| WO | 2015195306 A2 | 12/2015 | |
| WO | 2016144615 A1 | 9/2016 | |
| WO | WO-2018081826 A1 * | 5/2018 | ......... A61B 5/04001 |

OTHER PUBLICATIONS

International Search Report and Written Option for PCT Application No. PCT/US2021/013699, mailed May 12, 2021, 12 pgs.

Lerman, Imanuel et al., "Noninvasive transcutaneous vagus nerve stimulation decreases whole blood culture-derived cytokines and chemokines: a randomized, blinded, healthy control pilot trial," Neuromodulation: Technolgoy at the Neural Interface, vol. 19, 2016, pp. 283-291.

Rivens, A. Shaw, et al.; "Treatment monitoring and thermometry for therapeutic focused ultrasound," International Journal of Hyperthermia, vol. 23, Iss. 2, pp. 121-139, Mar. 2007.

* cited by examiner

| | 100% PUSH PULSE | 50% PUSH PULSE | SHEAR TRACKING PULSES | B-MODE IMAGING PULSES |
|---|---|---|---|---|
| PULSE DURATION | 800μs | 800μs | 81.5μs | 0.7μs |
| CENTER FREQUENCY | 2.2MHz | 2.2MHz | 3.5MHz | 1.75MHz |
| EXCITATION VOLTAGE | 75V | 37.5V | 61V | 102V |
| ESTIMATED TISSUE DISPLACEMENT | ~20μm | 5μm | <5nm | <5nm |
| PULSE REPETITION FREQUENCY (Hz) | 1 | 4 | 160 | 4092 |
| MECHANICAL INDEX | 1.4 | 0.85 | 0.23 | 1.42 |
| ISPTA.3 (mW/cm2) | 290.4 | 368.4 | 14.1 | 37.6 |
| GROUP 1 (SINGLE SITE) | | | | X |
| GROUP 2 (SINGLE SITE) | | X | X | X |
| GROUP 3 (SINGLE SITE) | X | | X | X |
| GROUP 4 (MULTI-SITE) | | | | X |
| GROUP 5 (MULTI-SITE) | | X | X | X |
| GROUP 6 (MULTI-SITE) | X | | X | X |

FIG. 11

NONINVASIVE TISSUE DISPLACEMENT CONTROL AND MONITORING FOR NEUROMODULATION

CROSS-REFERENCE TO RELATED APPLICATION

This application claims priority to and the benefit of U.S. patent application Ser. No. 16/750,932, entitled "NONINVASIVE TISSUE DISPLACEMENT CONTROL AND MONITORING FOR NEUROMODULATION", filed Jan. 23, 2020, which is herein incorporated by reference in its entirety.

BACKGROUND

The subject matter disclosed herein relates to techniques to target and/or dose regions of interest in a subject via application of neuromodulating energy to cause targeted physiological outcomes. In particular, the disclosed techniques may monitor and/or control ultrasound-induced tissue displacement as a result of a neuromodulation treatment.

Neuromodulation has been used to treat a variety of clinical conditions. For example, electrical stimulation at various locations along the spinal cord has been used to treat chronic back pain. However, positioning electrodes at or near the target nerves is challenging. For example, such techniques may involve surgical placement of the electrodes that deliver the energy. In addition, specific tissue targeting via neuromodulation is challenging. Electrodes that are positioned at or near certain target nerves mediate neuromodulation by triggering an action potential in the nerve fibers, which in turn results in neurotransmitter release at a nerve synapse and synaptic communication with the next nerve. Such propagation may result in a relatively larger or more diffuse physiological effect than desired, as current implementation of implanted electrodes stimulate many nerves or axons at once. Because the neural pathways are complex and interconnected, a more selective and targeted modulated effect may be more clinically useful. However, identification of effective energy application parameters that deliver energy to a desired region of interest and that cause desired physiological outcomes is complex given individual variability in patient anatomy and clinical responses.

BRIEF DESCRIPTION

The disclosed embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, a neuromodulation delivery system is provide that includes an energy application device configured to deliver neuromodulating energy to a region of interest of an internal tissue in a subject. The system also includes a controller configured to control application of the neuromodulating energy via the energy application device to the region of interest to deliver a dose of the neuromodulating energy thereto; receive image data of the region of interest during and/or after the application of the neuromodulating energy; identify a change in a molecule of interest in the subject relative to a baseline acquired at or before the application of the neuromodulating energy as a result of the application of the neuromodulating energy; and determine a tissue displacement of the region of interest associated with the change in the molecule of interest, wherein the tissue displacement is determined based on the image data.

In one embodiment, a neuromodulation delivery system is provide that includes an ultrasound probe configured to deliver neuromodulating energy to a region of interest of an internal tissue in a subject via a therapy transducer and acquire image data of the region of interest via an imaging transducer. The system also includes a controller configured to control application of the neuromodulating energy via the therapy transducer of the ultrasound probe to the region of interest to deliver a dose of the neuromodulating energy thereto, wherein the therapy transducer is controlled under control parameters; receive image data of the region of interest acquired by the imaging transducer of the ultrasound probe during the application of the neuromodulating energy; determine tissue displacement of the region of interest during the application of the neuromodulating energy based on the image data; and modify one or more control parameters of the therapy transducer based on the determined tissue displacement or based on a change in a concentration of a molecule of interest in the subject relative to a baseline concentration acquired at or before the application of the neuromodulating energy.

In another embodiment, a method is provided that includes the steps of delivering a reference pulse to a region of interest of a subject via an energy application device; delivering a therapy pulse to the region of interest via the energy application device subsequent to delivering the reference pulse; delivering a tracking pulse to the region of interest via the energy application device subsequent to delivering the therapy pulse; identifying a phase change between the reference pulse and the tracking pulse; and determining a tissue displacement in or near the region of interest based on the phase change.

In another embodiment, a method is provided that includes the steps of delivering a reference pulse to a region of interest of a subject via an energy application device; delivering a therapy pulse to the region of interest via the energy application device subsequent to delivering the reference pulse; delivering a tracking pulse to the region of interest via the energy application device subsequent to delivering the therapy pulse; identifying a change in concentration of a molecule of interest relative to a baseline and as a result of delivering the therapy pulse; and determining a tissue displacement in or near the region of interest that is associated with the change in concentration based on the phase change

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 11 shows experimental control parameters for ultrasound energy application to human subjects of FIGS. 13-16;

DETAILED DESCRIPTION

Figure 1:
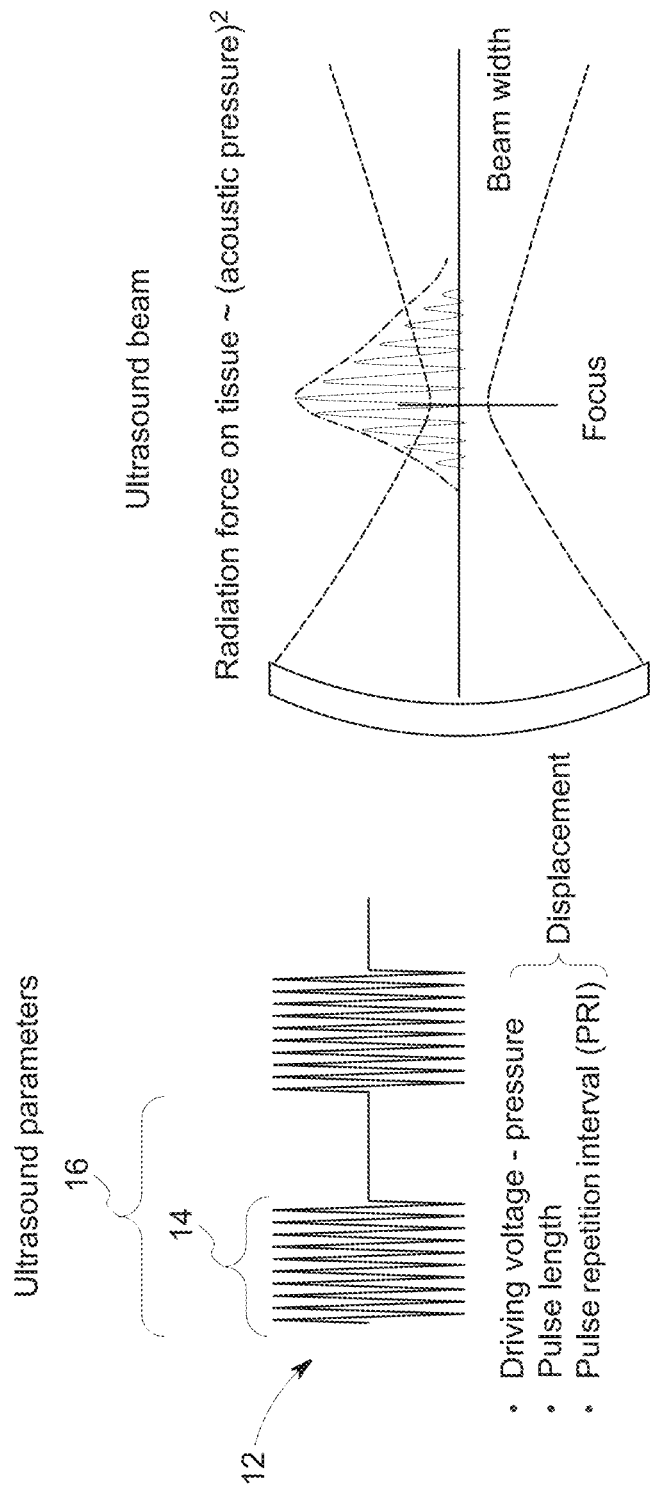
FIG. 1 is a schematic representation of ultrasound parameters and ultrasound radiation force on tissue according to embodiments of the disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," "in certain embodiments," "in some embodiments," and "in one (an) embodiment."

Neuromodulation within tissues may be achieved by local mechanical stress/strain, which stretches or displaces tissues and activates different intra-cellular and inter-cellular processes in response. Provided herein are techniques to control and/or to monitor the amount of stretch and/or displacement caused by neuromodulating energy application, e.g., noninvasive ultrasound. By controlling and monitoring the amount of stretch and/or displacement within specific tissues that are targeted for neuromodulating energy, the control parameters of a neuromodulation energy dose may be adjusted to produce different levels of effect and/or different types of effects. In an example, controlling the dose of the amount of stretch and/or the amount of displacement varies the level of anti-inflammatory effects in certain neuromodulating protocols in humans. Further, the amount of stretch and/or displacement induced by ultrasound energy may be noninvasively measured also using ultrasound (e.g., using a combination probe) to provide feedback for real-time quantification and precision control of the delivered dose.

Displacement in tissue in response to the radiation force of focused ultrasound may, in certain embodiments, be assessed using shear-wave (elastography) imaging. The present disclosure demonstrates that a threshold effect is observed in living organisms whereby small amounts of displacement (sub-threshold displacements) do not produce a neuromodulated effect and larger amounts of displacement (supra-threshold) produce a neuromodulated effect. A second threshold effect is observed in living organisms where large amounts of displacement (over-exposure) produce undesired effects and the intended neuromodulation effect is absent or diminished. That is, the control parameters of a dose may be adjusted for each patient to achieve a desired tissue displacement. In addition to identifying plateau or maximal displacement levels associated with particular control parameters, the tissue area over which the displacement is applied and the time-varying nature of the displacement are observed in the disclosed embodiments to produce different neuromodulation effects. This spatial-temporal relationship and the total duration of the applied dose has been shown as provided in the present disclosure to produce different levels of neuromodulation in living organisms.

Producing an appropriate amount of stretch and/or displacement in different individuals is challenging due to variations in individual anatomy and variations in individual tissue properties. That is, a liver may respond differently than a pancreas. Measuring and monitoring the amount of stretch and/or displacement during a neuromodulating energy dose may be used to minimize deviations from optimal dosage for an individual patient. Measuring and monitoring in real-time allows for more precise control of the temporal aspects of the applied stretch and/or displacement. Measuring and monitoring over a size-varying tissue region allows for more precise control of the spatial aspects of the applied stretch and/or displacement. For example, a particular region of interest for energy application may be selected or monitored for desired tissue displacement. In certain embodiments, the present techniques facilitate determining an appropriate or target amount of spatial-temporal stretch and/or displacement for a specific individual (personalized) and more reliably producing that determined amount of spatial-temporal stretch and/or displacement over multiple time scales. Accordingly, assessing tissue displacement during and after application of neuromodulating energy may permit fine-tuning of energy parameters to not only generate targeted physiological outcomes, but to account for patient to patient variability in responsiveness and tissue variability in responsiveness (inter and/or intra tissue).

Stretch and/or displacement may be induced into tissues in multiple ways. The disclosed embodiments are discussed in the context of noninvasive ultrasound, which permits controlled focus and shape of energy applied to a region of interest while simultaneously penetrating deeply into tissue. FIG. 1 is a schematic representation of an ultrasound beam, denoting the focus point, and a detailed view of the applied ultrasound energy, showing characteristics of amplitude and frequency 12, pulse high-time or pulse length 14, and pulse repetition interval 16. The present techniques demonstrate that modifications to the driving voltage (applied pressure) that produces the ultrasound waves as well as to the pulse length and the pulse repetition interval generates measurable physiological effects that are correlated to tissue displacement. In certain disclosed embodiments, the effects of a full amplitude and half amplitude driving voltage are compared. In addition, changes to the pulse length and pulse repetition interval are assessed.

Figure 2:
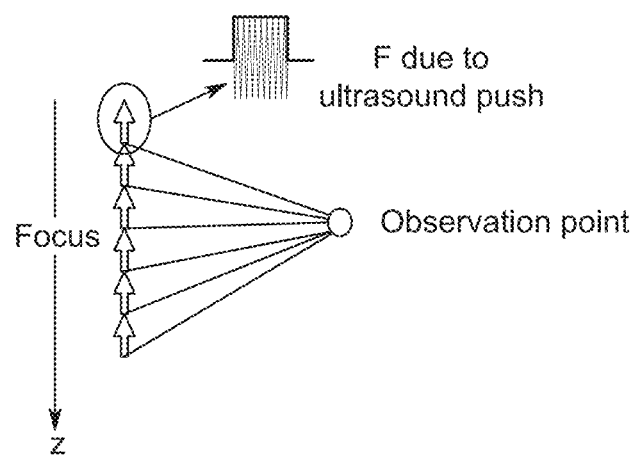
FIG. 2 is a schematic representation of a tissue displacement model as a result of ultrasound radiation force on tissue according to embodiments of the disclosure.
Figure 3:
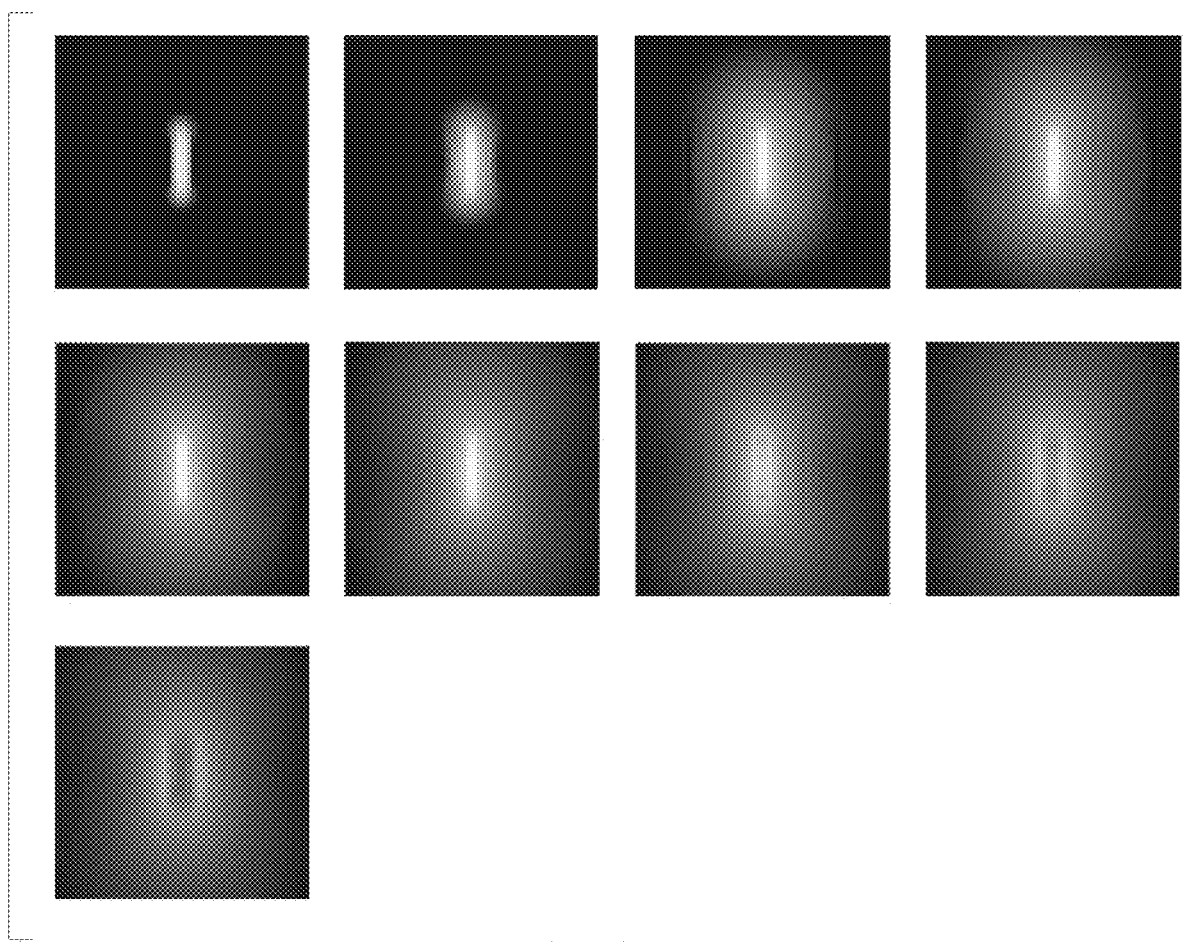
FIG. 3 shows images obtained from tissue that are indicative of ultrasound-induced tissue displacement.

FIG. 2 is a simplified tissue displacement model showing displacement assuming that the ultrasound focus is a simple line source with uniformly distributed displacement in the z direction. The model also assumes that the tissue is an attenuating, homogenous, elastic medium. The model permits calculation of displacement F at any observation point in 2D tissue F (x,y,t). Each arrow represents an applied pulse. FIG. 3 is a time series of ultrasound images starting at time point zero and taken over 4 milliseconds showing displacement over a 20 mm×20 mm region, using a line source assumption with a diameter 10 mm long and a total push pulse over 3 milliseconds. Each individual image represents the displacement over 0.5 milliseconds; at every 0.5 milliseconds, an additional 500 microsecond pulse (shown as a yellow arrow in FIG. 2) is applied to the tissue. The displacement shown is log scaled with a 30 dB display range. The ultrasound images demonstrate displacement in tissue of several micrometers over the time that the 3 millisecond total pulse was applied.

Figure 4:
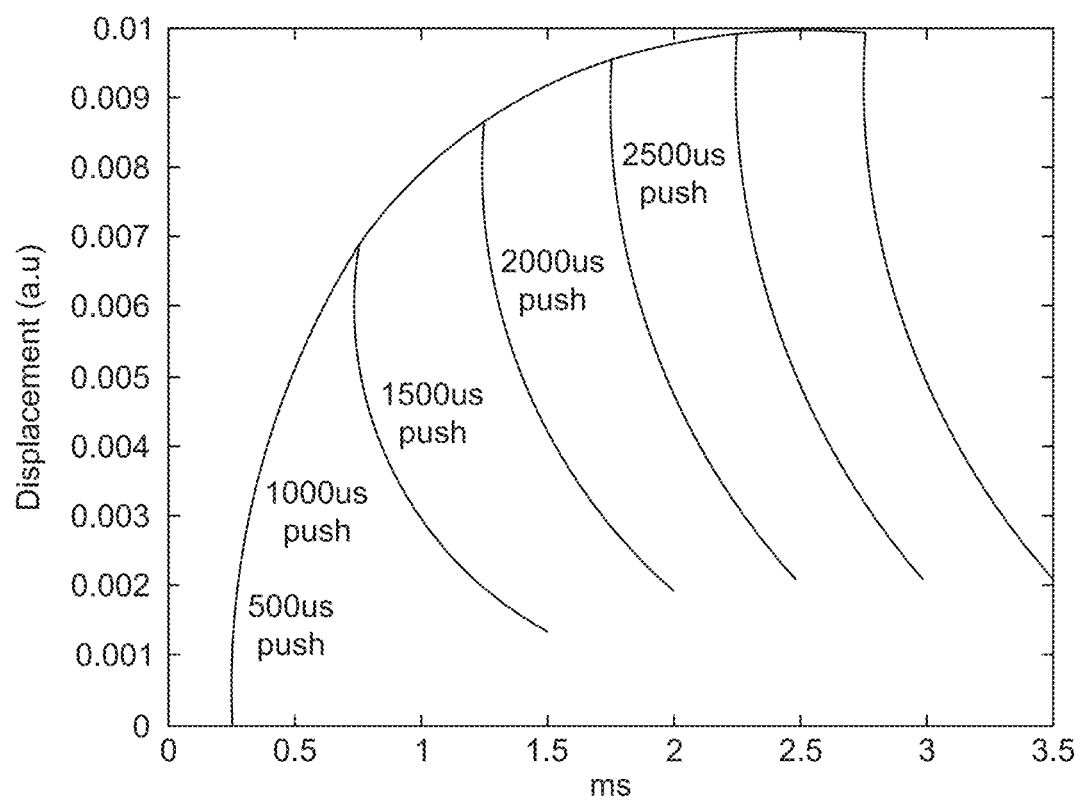
FIG. 4 shows a relationship between displacement distance and a pulse time of ultrasound radiation force on tissue according to embodiments of the disclosure.

FIG. 4 shows the observed relationship between displacement and pulse length for the displacement in the images of FIG. 3. Over time, as the total pulse increases (total dose delivery of multiple pulses) with each 500 microsecond pulse length push, a larger displacement is observed until all the displacement contributed from the source cannot add up coherently. Thus, the displacement amplitude (shown as arbitrary units) plateaus. In the depicted example, the pulse push is additive 500 microsecond pulses with no relaxation period. Accordingly, as provided herein, a pulse length and/or total pulse high-time over the course of a dose time period may be selected to achieve a maximum and/or plateau value potential tissue displacement for a particular driving voltage (and for a particular region of interest) at a lower range of plateau pulse length values, thus minimizing ultrasound energy exposure at the region of interest over the course of the applied dose, which may lead to more targeted effects. Accordingly, in an embodiment, the present techniques may track displacement in real time over dose delivery, calculating a rate of change of tissue displacement. Upon determining that the rate of change is decreasing (e.g., falls below a selected threshold), indicating an approaching plateau, a controller of the ultrasound probe may automatically modify energy delivery. For example, the controller may cease energy delivery or may modify control parameters to move out of the plateau portion of the curve. Such tracking may be desirable, because minimizing ultrasound energy exposure may prevent or delay compensating mechanisms in the tissue, preserving the region of interest as an appropriate therapy site for a longer period of time. Further, by avoiding the plateau portion of the curve of FIG. 4, undesired additional physiological effects of the therapy may not be activated.

Figure 5:
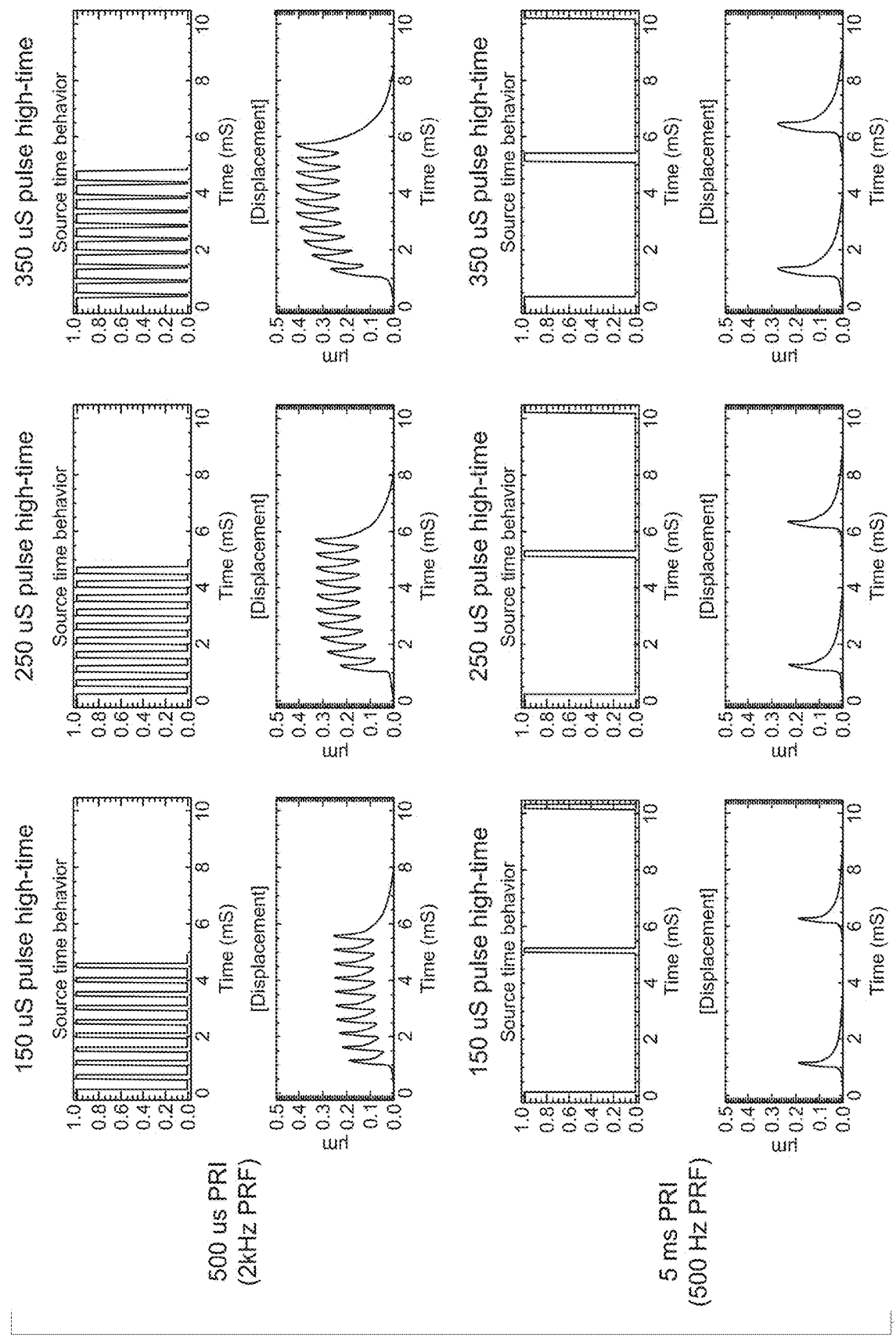
FIG. 5 shows a relationship between displacement distance and a pulse time of ultrasound radiation force on tissue according to embodiments of the disclosure.

However, as provided herein, other control parameters of ultrasound dose delivery may be modified to achieve desired physiological outcomes associated with characteristic tissue displacements and/or relaxation. For example, as shown in FIG. 5, a pulse repetition interval of 500 microseconds (at 2 KHz PRF) or 5 millisecond pulse repetition interval (500 Hz PRF) may vary in a pulse length "on" or pulse high-time, with accompanying variation in resulting tissue displacement. For example, an increased amount of pulse high-time at the same PRF results in overall greater displacement over the course of 10 milliseconds at both higher (2 kHz) and lower (500 Hz) frequency settings. That is, the 150 microsecond pulse high-time results in less displacement of tissue than the 350 microsecond on time. Accordingly, an ultrasound therapy transducer may be tuned to vary a pulse high-time within a pulse repetition interval to change the profile of tissue displacement. In addition, increasing the pulse repetition interval may also permit relaxation between pulses, which in turn changes the effects of compounding displacement over the dose. The 5 millisecond pulse repetition interval for 150, 250, and 350 microsecond pulse on times permits near-total relaxation, while the shorter 500 microsecond pulse repetition interval permits less than complete relaxation. In this manner, the pulses in the 500 microsecond pulse repetition interval demonstrate compounding displacement effects over time that disappear once the dose is halted. As provided herein, the present techniques permit ultrasound dose therapy protocols with control parameters for energy delivery that tune the driving voltage, frequency, pulse length, and pulse repetition interval, and/or overall dose delivery time. For example, the overall energy delivered to a region of interest observed for the conditions the top panels (500 microseconds PRI at 2 KHz PRF) than the conditions for the lower panels (5 millisecond PRI at 500 Hz PRF). The estimated displacement may be assessed or estimated as an area under the curve over the dose delivery period, and the control parameters may be programmed to fall within desired area under the curve values of tissue displacement for a particular region of interest.

Figure 6:
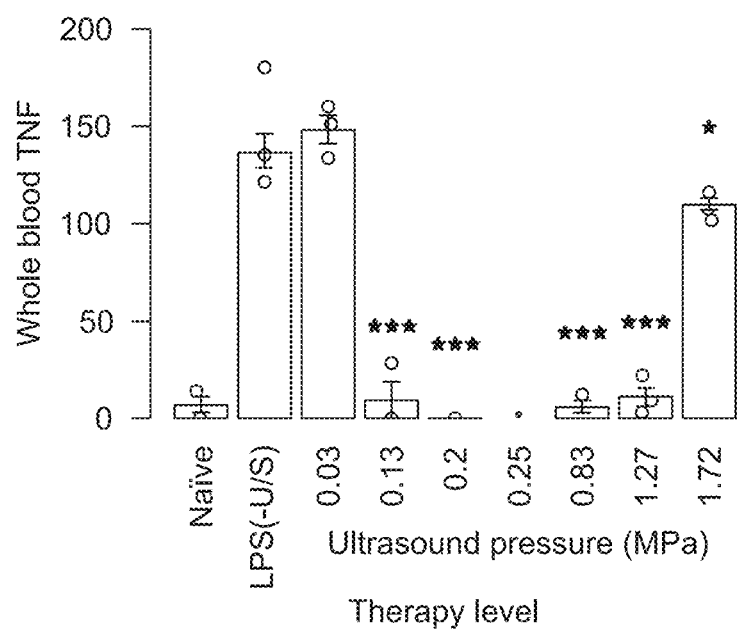
FIG. 6 shows effects on whole blood tumor necrosis factor (TNF) levels for different applied pressures of ultrasound to the spleen in an LPS-exposed animal model.

The present techniques target tissue displacement caused by neuromodulation that is tied to targeted physiological outcomes. FIG. 6 shows varying effects of ultrasound pressure (mPa) applied to the spleen on whole blood TNF for an LPS-exposed animal model. The amount of displacement caused by ultrasound is a function of the elastic properties of the tissue and the characteristics of the applied energy, such as how long the push (pulse length, pulse repetition interval) and/or how hard (temporal average intensity $mW/cm^2$ and/or peak pressure mPa) the push. The displacement reaches a maximum where the force exerted by the ultrasound equals the force pushing back by the tissue. Once at this maximum, pushing longer does not make any more displacement. Pushing harder (e.g. more pressure) is a way to get more displacement (reach a new maximum). In the case shown in FIG. 6 for an LPS-exposed animal model with resulting inflammation and associated baseline increases in TNF, the time duration of the push was kept the same but the amount of pressure was varied. Two threshold effects were observed, one with little physiological effect (too low pressure at 0.03 mPa) and a second threshold where the physiological effect goes away (too high pressure at the 1.72 mPa bar). However, the data between the thresholds shows that the increase in whole blood TNF associated with LPS exposure was reversed for certain ultrasound pressures while being unaffected at too high or too low pressures. Accordingly, as provided herein, the present techniques may permit identifying ultrasound pressures that lie between thresholds associated with no physiological effects and/or applying ultrasound energy within the range of these identified pressures. As provided herein, tissue displacement caused by ultrasound energy may be used as a marker for desired physiological effects. In an embodiment, the change in effect between the 1.27 mPa bar and the 1.72 mPA bar is associated with a physical change in tissue reaction to applied ultrasound energy from stretch displacement to heat/cavitation at higher pressures. The desired effects may be observed at the pressures associated with stretch displacement. Accordingly, control parameters for an ultrasound dose may be selected to cause stretch displacement and may avoid peak pressures that are too low to cause displacement or that are so high that the dominant tissue effects in or near the region of interest are heat/cavitation.

Figure 7:
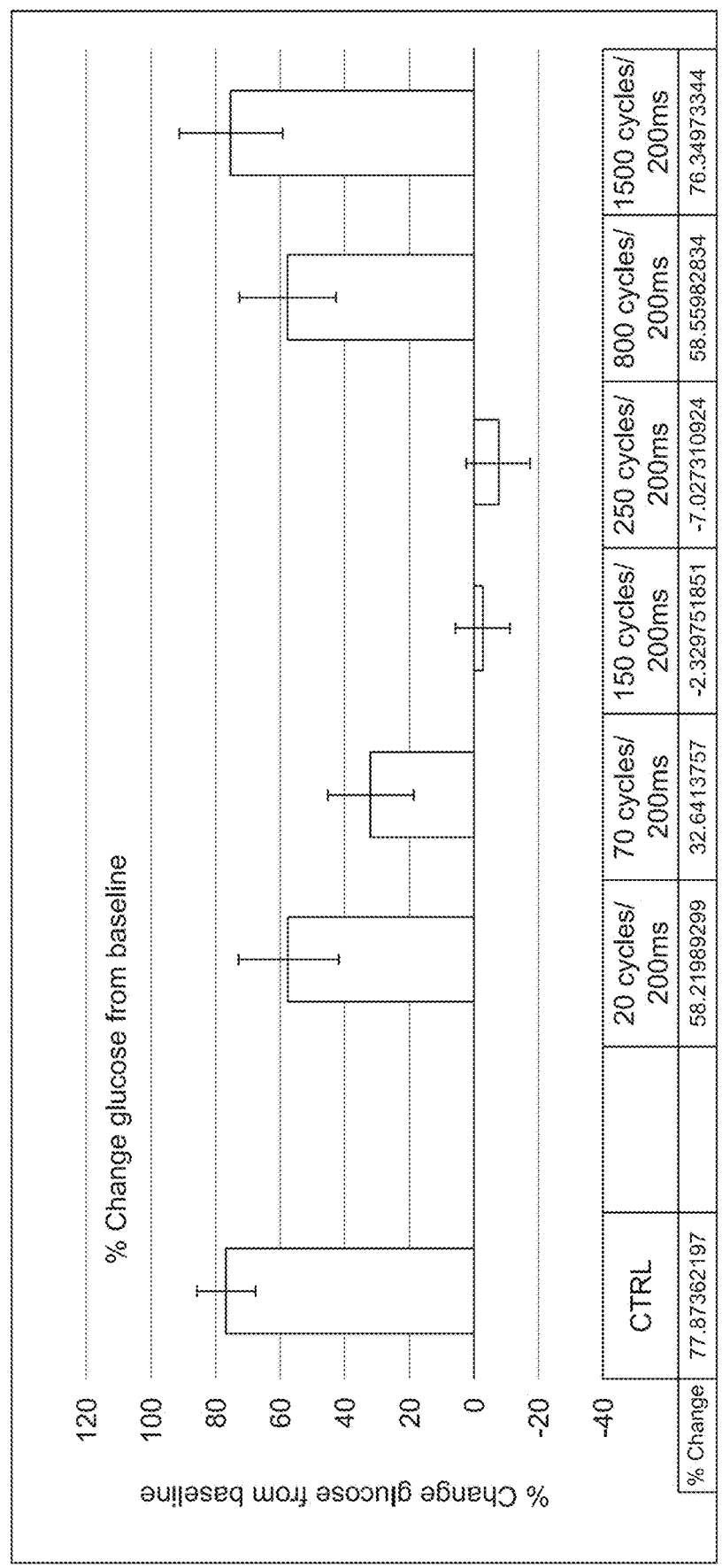
FIG. 7 shows effects on glucose levels for different pulse lengths of ultrasound applied to the spleen in an LPS-exposed animal model.

FIG. 7 shows results of changing time duration for a pressure of the push (pulse) kept the same (200 milliseconds) relative to a control for glucose changes relative to baseline. The results show two threshold effects, one with little physiological effect (too short a duration) and a second threshold where the physiological effect goes away (too long a duration). Accordingly, the control parameters may be selected to align with tissue displacement associated with the desired change in glucose percentage.

Figure 8:
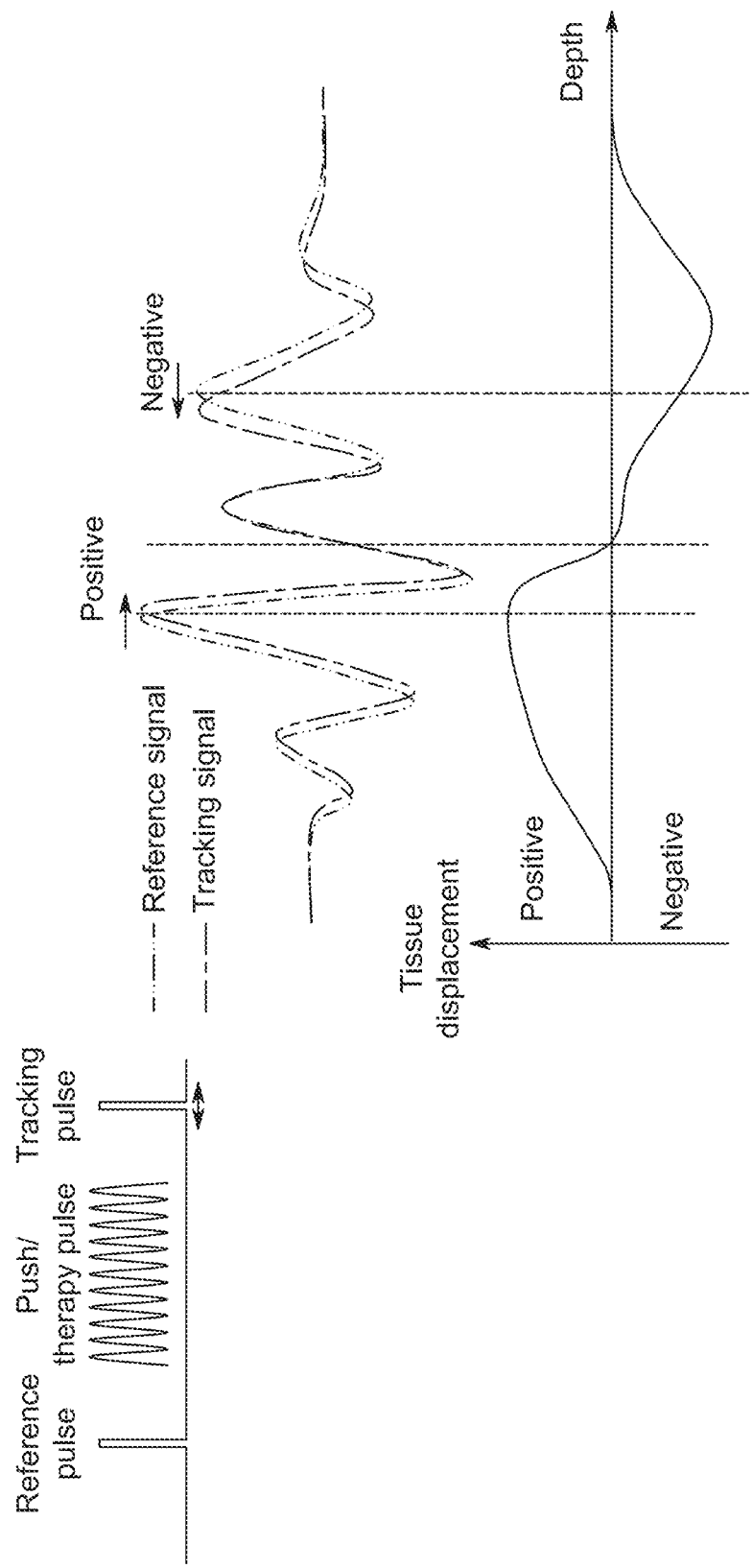
FIG. 8 is a schematic representation of a phase change in a reference and tracking pulse used to determine tissue displacement according to embodiments of the disclosure.

To that end, the present techniques provide systems and methods for monitoring and/or assessing tissue displacement. In an embodiment, the tissue displacement may be assessed via ultrasound. In one embodiment, an ultrasound probe may be a combination probe that includes a therapy transducer and an assessment (imaging) transducer. The imaging transducer may be used to identify and select a region of interest as well as to track displacement of tissue caused by application of neuromodulating energy. FIG. 8 shows an example control or drive signal for identifying tissue displacement that may be used to control an ultrasound probe to deliver therapy and track associated tissue effects. In an embodiment, a short reference imaging pulse and a tracking pulse bracket a therapy pulse. A phase change between reference and tracking signals based on the ultrasound image data is used calculate tissue displacement. As shown, the displacement may be in the positive or negative direction along an axis, and a total displacement, or area under the curve, may be used as a displacement metric.

Figure 9:
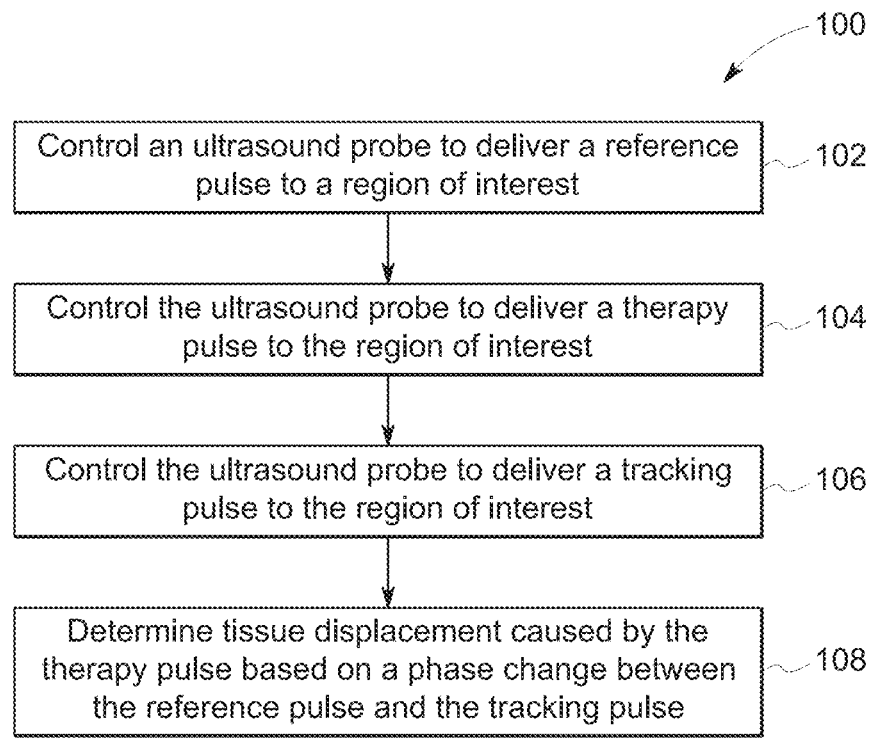
FIG. 9 is a flow diagram of a technique for determining tissue displacement according to embodiments of the disclosure.

FIG. 9 is a flow diagram of a method 100 for assessing tissue displacement as a result of ultrasound energy application to a region of interest in a target internal tissue. In the method 100, a transducer of an ultrasound probe delivers a reference imaging pulse to the region of interest and collects reflected ultrasound waves from the tissue to generate baseline or reference data (block 102), which is received by a controller of the ultrasound probe (e.g., an ultrasound system). A same ultrasound transducer of the ultrasound probe or a different ultrasound transducer (e.g., a dedicated therapy transducer) is controlled to apply an ultrasound therapy pulse (block 104). The ultrasound therapy application causes tissue displacement in or near the region of interest, which is identified using a tracking pulse delivered subsequent to applying the ultrasound energy (block 106). The reflected waves from the tracking pulse generate tracking data. The tracking data and the reference data are used to determine tissue displacement caused by the ultrasound energy pulse (block 108).

In certain embodiments, the control parameters of the reference and tracking pulses are selected such that they are short and sufficiently low energy to cause minimal or no displacement of the tissue. That is, the identified displacement is caused by the therapy pulse and not by the reference/tracking pulses. In certain embodiments, tracking pulses are emitted between pulse intervals, such that displacement is tracked for every pulse applied. In this manner, compounding displacement may be tracked until plateau values are reached. Further, displacement may be determined in realtime, to permit adjustment or modification of therapy pulse control parameters.

The relationship between tissue displacement and physiological effects as a result of neuromodulating ultrasound therapy was examined for 60 human subjects. The subjects were randomly assigned to one of six groups (n=10 for each group). As disclosed herein, ultrasound was used to cause tissue displacement vibrations of a region of interest of a target internal tissue. Groups of human subjects received a sham control ultrasound dose, a half amplitude dose of 115 $W/cm^2$ (Isppa spatial-peak pulse average intensity), or a full amplitude dose of 362 $W/cm^2$ (Isppa). The temporal average power (Ispta) for the 50% amplitude (368 $mW/cm^2$) is higher than the 100% amplitude (290 $mW/cm^2$) because it pushed more frequently. The ultrasound dose for the subjects receiving ultrasound energy was applied to a single site (Groups 1-3) or distributed between multiple sites (Groups 4-6).

Figure 10:
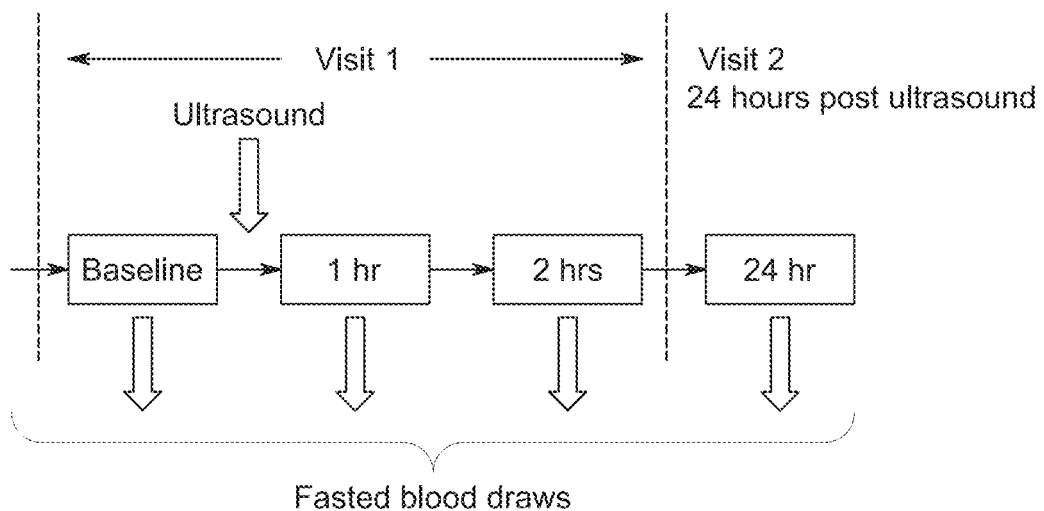
FIG. 10 shows an experimental timeline for ultrasound energy application to human subjects of FIGS. 13-16.
Figure 12:
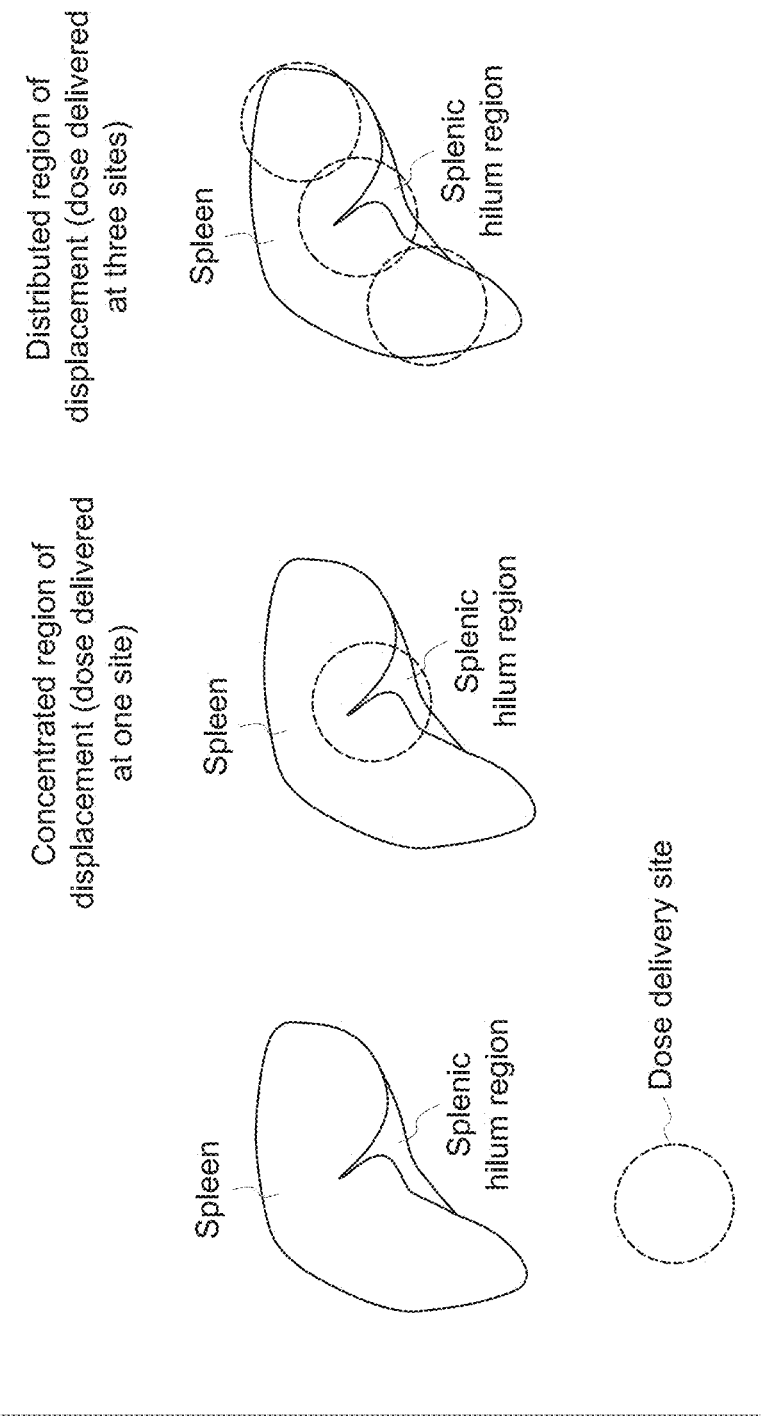
FIG. 12 shows concentrated and distributed regions of interest for ultrasound energy application to human subjects of FIGS. 13-16.

FIG. 10 shows the experimental protocol for each subject. For those human subjects receiving ultrasound, the therapy dose was delivered after fasted blood draws for baseline levels of various blood molecules, such as TNF, cytokines (IL-1, IL-6, IL-8, IL-10), glucose, and norepinephrine. TNF response of blood cells to LPS was assessed by performing a LPS assay on blood from a venous blood draw. The blood was exposed to LPS at concentrations of 0, 0.1, 1, 10, and 100 ng/ml followed by analysis of each sample with human TNF ELISA. The area under the curve (AUC) for the TNF response concentration across the five LPS concentrations was computed and used to characterize the TNF response of blood cells. Ultrasound energy was applied to a region of interest in a spleen tissue of each subject. Fasted blood draws were performed at 1 hr, 2 hrs, and 24 hrs after therapy dose. FIG. 11 summarized the control parameters and resulting tissue displacement for subjects in reach of the different groups. FIG. 12 is a schematic representation of the single site vs. multi-site delivery for the spleen.

Figure 13:
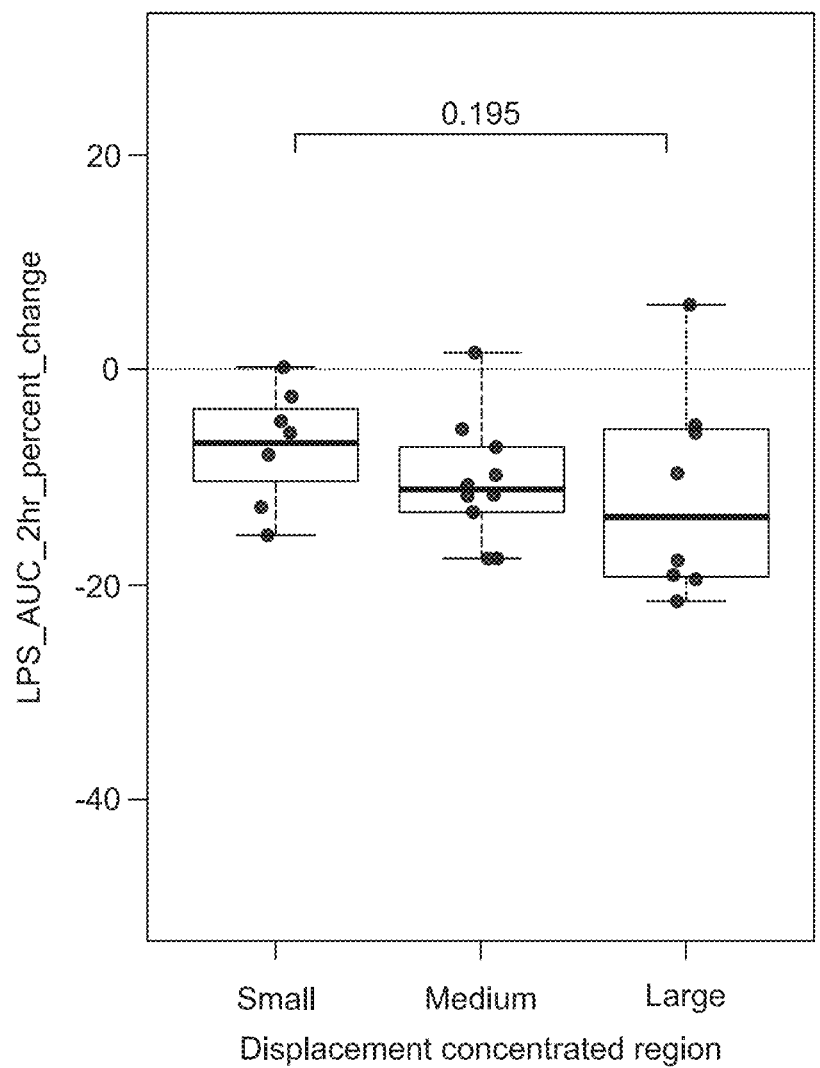
FIG. 13 shows a comparison of TNF response relative to degrees of tissue displacements associated with application of ultrasound energy.

FIG. 13 shows results of splenic ultrasound stimulation within a concentrated (single-site) region of interest. Larger displacement is correlated to greater reduction in TNF response of blood cells to LPS at 2 hours post stimulation. The top bracket shows the P-value (Wilcoxon test) comparing small and large displacement within a single or concentrated treatment region of interest. The data shown is from 8 subjects of Group 1 (Small Displacement), 10 subjects of Group 2 (Medium Displacement), and 8 Subjects of Group 3 (Large Displacement).

Figure 14:
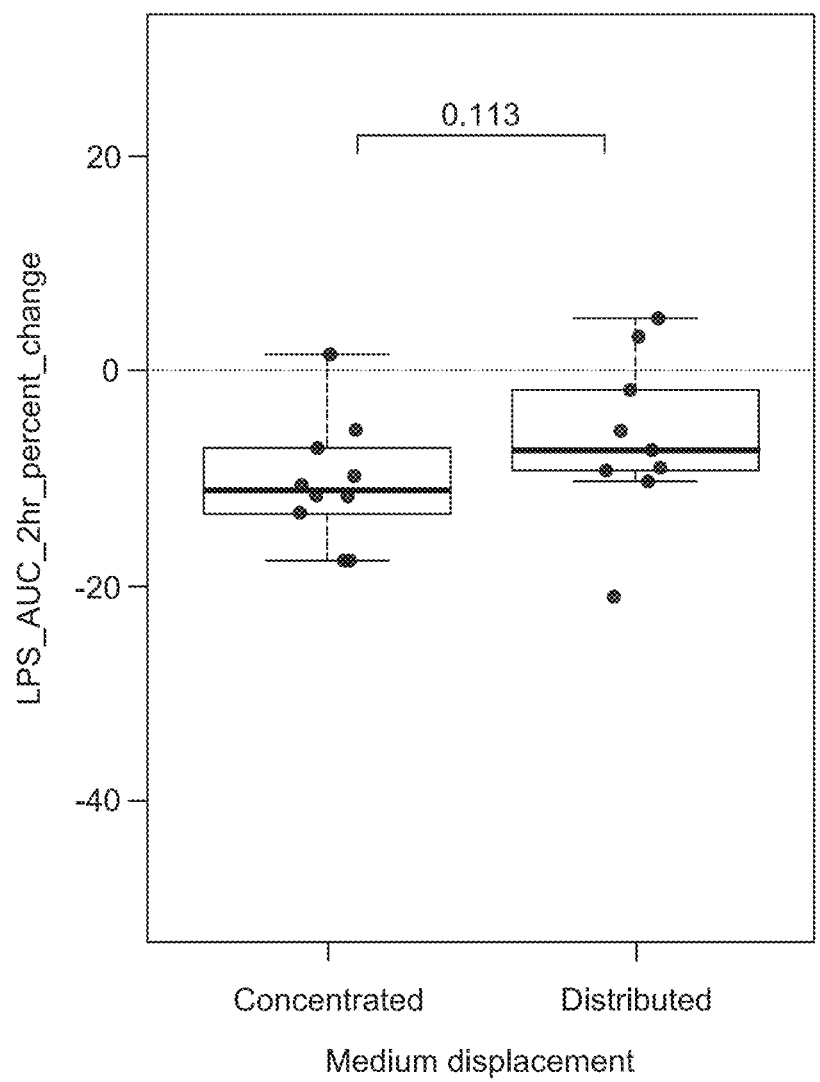
FIG. 14 shows a comparison of TNF response for displacements associated with concentrated and distributed application of ultrasound energy.

FIG. 14 shows a comparison between tissue displacement between concentrated (single site) and distributed (multi-site) ultrasound energy application for medium displacement groups. For medium displacement within a concentrated region, splenic ultrasound stimulation tends to cause greater reduction in TNF response of blood cells to LPS at 2 hours post stimulation. The top bracket shows the P-value (Wilcoxon test) comparing medium displacement within a concentrated vs. distributed region. The data shown is from 10 subjects of Group 2 (Medium Displacement) and 9 subjects of Group 5 (Medium Displacement).

Figure 15:
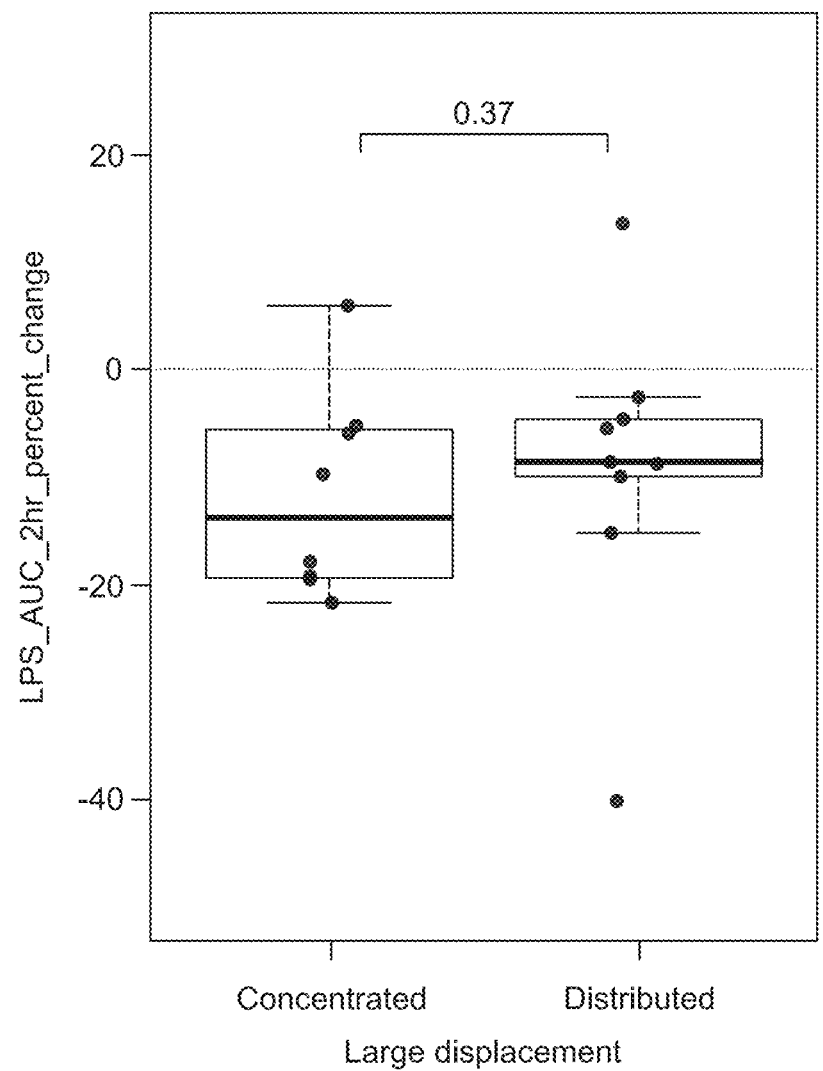
FIG. 15 shows a comparison of TNF response for displacements associated with concentrated and distributed application of ultrasound energy.

FIG. 15 shows a comparison between tissue displacement between concentrated (single site) and distributed (multi-site) ultrasound energy application for large displacement groups. For large displacement within a concentrated region, splenic ultrasound stimulation tends to cause greater reduction in TNF response of blood cells to LPS at 2 hours post stimulation. The top bracket shows the P-value (Wilcoxon test) comparing large displacement within a concentrated vs. distributed region. The data shown is from 8 subjects of Group 3 (Large Displacement) and 9 subjects of Group 6 (Large Displacement).

Figure 16:
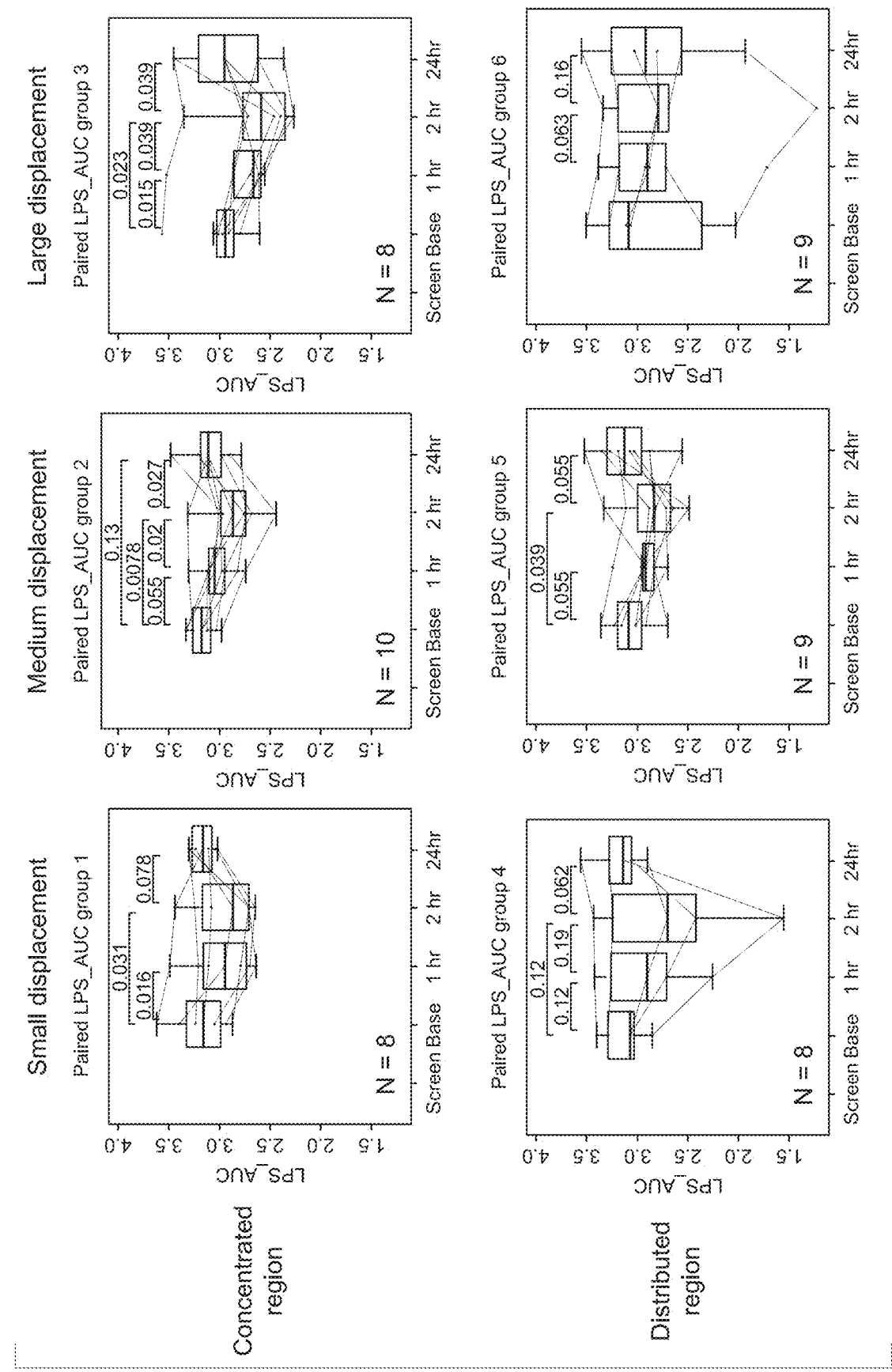
FIG. 16 shows a summary of TNF response and displacement at different time points.

FIG. 16 is a summary of TNF response in the six subject groups. The top panels show the TNF change for the single-site energy application, and the bottom panels show the TNF change for distributed energy application. The results show that changes to the applied pressure or power between groups 2 and 3 were associated with significant changes in TNF response relative to baseline. The study groups also show a return to baseline TNF levels at 24 hours.

As shown, changes in ultrasound energy application control parameters and region of interest selection affects physiological outcomes in a manner that is linked to degrees of tissue displacement. While the experimental results showed changes in TNF relative to baseline as a result of ultrasound energy application (e.g., ultrasound therapy), it should be understood that these results are presented by way of example. The present techniques may induce and assess a presence or level of tissue displacement in a region of interest that is associated with a desired physiological outcome, such as a change in concentration of a molecule of interest relative to a baseline level before treatment. Rather than or in addition to tracking the change in the molecule concentration, the present techniques may assess tissue displacement to determine that neuromodulation ultrasound therapy is effective.

Figure 17:
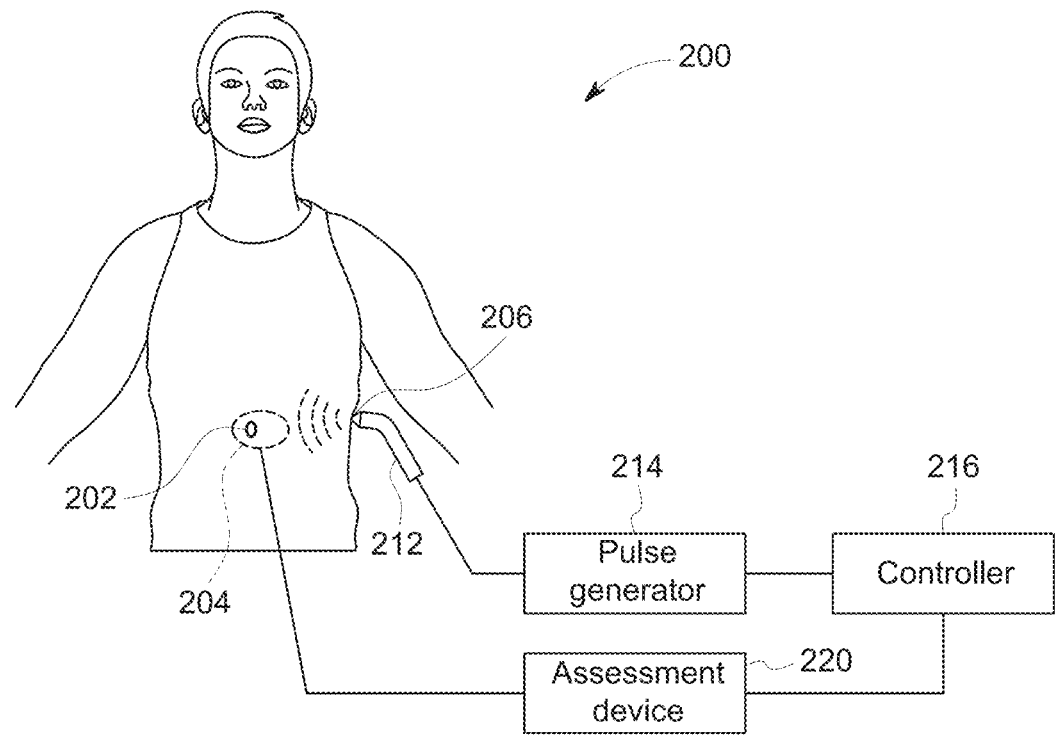
FIG. 17 is a schematic representation of an ultrasound neuromodulation system according to embodiments of the disclosure.

FIG. 17 shows a system 200, e.g., a neuromodulation delivery system, for neuromodulation to achieve neuromodulating effects such as tissue displacement at one or more regions of interest 202 of a target tissue 204 associated with neurotransmitter release and/or activation of components (e.g., the presynaptic cell, the postsynaptic cell) of a synapse in response to an application of energy. The depicted system includes a pulse generator 214 coupled to an energy application device 206. The energy application device 206 is configured to receive energy pulses, e.g., via leads or wireless connection, that in use are directed to multiple regions of interest 20 in one or more internal tissues or organ/s of a subject, which in turn results in a targeted physiological outcome.

In certain embodiments, the energy application device 206 and/or the pulse generator 214 may communicate wirelessly, for example with a controller 216 that may in turn provide instructions to the pulse generator 214. In other embodiments, the energy application device 206 may be an extracorporeal device, e.g., may operate to apply energy transdermally or in a noninvasive manner from a position outside of a subject's body, and may, in certain embodiments, be integrated with the pulse generator 214 and/or the controller 16. In embodiments in which the energy application device 206 is extracorporeal, the energy application device 206 may be operated by a caregiver and positioned at a spot on or above a subject's skin such that the energy pulses are delivered transdermally to a desired internal tissue. Once positioned to apply energy pulses to the desired region or regions of interest 202, the system 200 may initiate neuromodulation of one or more nerve pathways to achieve targeted physiological outcome or clinical effects. In other embodiments, the pulse generator 14 and/or the energy application device 206 may be implanted at a biocompatible site (e.g., the abdomen) and may be coupled internally, e.g., via one or more leads. In some embodiments, the system 200 may be implemented such that some or all of the elements may communicate in a wired or wireless manner with one another.

In certain embodiments, the system 200 may include an assessment device 220 that is coupled to the controller 216 and that assesses characteristics that are indicative of whether the targeted physiological outcome of the modulation have been achieved. In one embodiment, the targeted physiological outcome may be local. For example, the modulation of one or more nerve pathways may result in local tissue or function changes, such as tissue structure changes, local change of concentration of certain molecules, tissue displacement, increased fluid movement, etc. The targeted physiological outcome may be a goal of the treatment protocol.

The modulation of one or more nerve pathways to achieve a targeted physiological outcome may result in systemic or non-local changes, and the targeted physiological outcome may be related to a change in concentration of circulating molecules or a change in a characteristic of a tissue that does not include the region of interest to which energy was directly applied. In one example, the displacement may be a proxy measurement for a desired modulation, and displacement measurements below an expected displacement value may result in modification of modulation parameters until an expected displacement value is induced. Accordingly, the assessment device 220 may be configured to assess concentration changes in some embodiments. In some embodiments, the assessment device 220 may be configured to assess tissue displacement. For example, the assessment device may be configured to use elastography techniques. Elastography may be used to examine tissue material properties. In the present techniques, elastography may be used to assess changes to tissue that are induced by an ultrasound therapy pulse or dosing protocol. While the depicted elements of the system 200 are shown separately, it should be understood that some or all of the elements may be combined with one another.

Based on the assessment, the modulation parameters of the controller 216 may be altered such that an effective amount of energy is delivered. For example, if a desired modulation is associated with a change in concentration (circulating concentration or tissue concentration of one or more molecules) within a defined time window (e.g., 5 minutes, 30 minutes after a procedure of energy application starts) or relative to a baseline at the start of a procedure, a change of the modulation parameters such as pulse frequency or other parameters may be desired, which in turn may be provided to the controller 216, either by an operator or via an automatic feedback loop, for defining or adjusting the energy application parameters or modulation parameters of the pulse generator 214 until the modulation parameters result in an effective amount of energy being applied. In one embodiment, an initially defined region of interest 202 may be refined to yield an updated region of interest 202 based on feedback from the assessment device as to the efficacy of the neuromodulating energy over the course of the treatment protocol. The feedback may be, for example, tissue displacement as a result of the application of neuromodulating energy. These refinements or updates to the region of interest may be used as part of patient-specific networks, where the network is updated to identify the specific region of interest that has the most impact on the physiological parameters of interest for that particular individual based on the desired clinical outcome.

The system 200 as provided herein may provide energy pulses according to various modulation control parameters as part of a treatment protocol to apply the effective amount of energy. For example, the modulation control parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The control parameters may also include frequency and duration of a stimulation application. The application frequency may be continuous or delivered at various time periods, for example, within a day or week. Further, the treatment protocol may specify a time of day to apply energy or a time relative to eating or other activity. The treatment duration to cause the targeted physiological outcomes may last for various time periods, including, but not limited to, from a few minutes to several hours. In certain embodiments, treatment duration with a specified stimulation pattern may last for one hour, repeated at, e.g., 72 hour intervals. In certain embodiments, energy may be delivered at a higher frequency, say every three hours, for shorter durations, for example, 30 minutes. The application of energy, in accordance with modulation parameters, such as the treatment duration, frequency, and amplitude, may be adjustably controlled to achieve a desired result.

Figure 18:
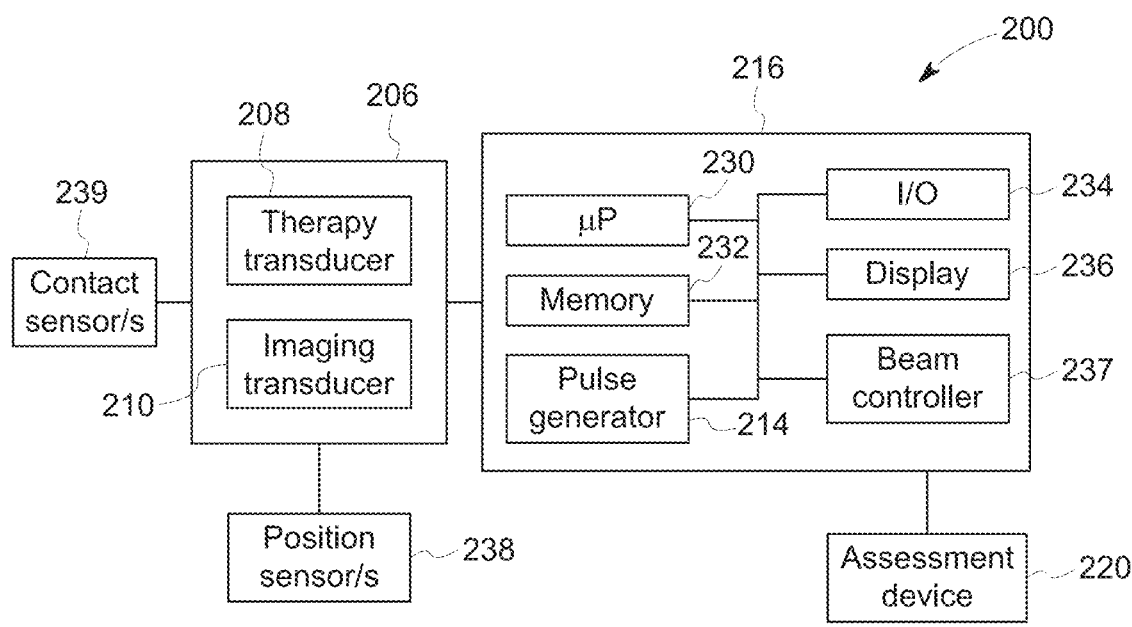
FIG. 18 is a block diagram of an ultrasound neuromodulation system according to embodiments of the disclosure.

FIG. 18 is a block diagram of certain components of the system 200. As provided herein, the system 200 for neuromodulation may include a pulse generator 214 that is adapted to generate a plurality of energy pulses for application to a tissue of a subject. The pulse generator 214 may be separate or may be integrated into an external device, such as a controller 216. The controller 216 includes a processor 230 for controlling the device. Software code or instructions are stored in memory 232 of the controller 216 for execution by the processor 230 to control the various components of the device. The controller 216 and/or the pulse generator 214 may be connected to the energy application device 206 via one or more leads or wirelessly.

The controller 216 may include a user interface with input/output circuitry 234 and a display 236 that are adapted to allow a clinician to provide selection inputs (e.g., selecting a region of interest 20 or a particular segment on an image of the target tissue that is associated with a desired region of interest 20) or control parameters to modulation programs. The processor 230 may be configured to control the energy application device and drive a therapy transducer 208 and/or an imaging transducer 210 as provided herein. Further, the processor 230 may be configured to determine tissue displacement based on data received from the imaging transducer 210.

The system may include a beam controller 237 that may control a focus location of the energy beam of the transducer 14 of the energy application device 206 by controlling one or both of steering and/or focusing of the energy application device 206 to apply treatment. The beam controller 237 may also control or one or more articulating portions of the energy application device 206 to reposition the transducer. The beam controller may receive instructions from the processor 230 to cause changes in focusing and/or steering of the energy beam. The system 200 may be responsive to position sensor/s 238 and/or contact sensor/s 239 that provide feedback on the energy application device 206. The beam controller 237 may include a motor to facilitate steering of one or more articulating portions of the energy application device 206. It is contemplated that the system 200 may include features to permit position, steering, and/or focus adjustments to facilitate the techniques disclosed herein.

Each modulation program stored in the memory 232 may include one or more sets of modulation parameters including pulse amplitude, pulse duration, pulse frequency, pulse repetition rate, etc. The pulse generator 214 modifies its internal parameters in response to the control signals from controller device 216 to vary the stimulation characteristics of energy pulses transmitted through lead 233 to a subject to whom the energy application device 206 is applied. Any suitable type of pulse generating circuitry may be employed, including but not limited to, constant current, constant voltage, multiple-independent current or voltage sources, etc. The energy applied is a function of the current amplitude and pulse duration. The controller 216 permits adjustably controlling the energy by changing the modulation parameters and/or initiating energy application at certain times or suppressing energy application at certain times. In one embodiment, the adjustable control of the energy application device 206 to apply energy is based on information related to a determined tissue displacement.

If the information is from the assessment device 220, a feedback loop may drive the adjustable control. For example, a diagnosis may be made based on tissue displacement, as measured by the assessment device 220, in response to neuromodulation. When the displacement is above a selected threshold or range, the controller 216 may initiate a treatment protocol of energy application to a region of interest (e.g., spleen) and with modulation parameters that are associated with a targeted physiological outcome, such as a reduction in circulating glucose. The treatment protocol may use different modulation parameters than those used in the diagnosis protocol (e.g., higher energy levels, more frequent application).

In one embodiment, the memory 232 stores different operating modes that are selectable by the operator. For example, the stored operating modes may include separate algorithms for identifying a particular region of interest and executing a set of modulation parameters associated with a particular treatment site, such as regions of interest in the liver, pancreas, gastrointestinal tract, spleen. Each organ or site may have different associated modulation parameters based on the depth of the relevant organ, the size of the region of interest, the desired physiological outcome, etc. Rather than having the operator manually input the modes, the controller 216 may be configured to execute the appropriate instruction based on the selection of a particular organ. In another embodiment, the memory 232 stores operating modes for different types of procedures. For example, activation may be associated with a different stimulating pressure or frequency range relative to those associated with depressing or blocking tissue function.

In a specific example, when the energy application device is an ultrasound transducer, the effective amount of energy may involve selected temporal average intensity applied to a region of interest. For example, the effective amount of energy may include a time-averaged power (temporal average intensity) and peak positive pressure in the range of 1 mW/cm$^2$-30,000 mW/cm$^2$ (temporal average intensity) and 0.1 MPa to 7 MPa (peak pressure). In one example, the temporal average intensity is less than 35 mW/cm$^2$, less than 500 mW/cm$^2$, or less than 720 mW/cm$^2$ in the region of interest. In an example, the temporal average intensity is associated with levels less than those associated with thermal damage and ablation/cavitation. The controller 216 may be capable of operating in a validating mode to acquire a selected treatment position and the selected treatment position may be implemented as part of a treatment operating mode that is configured to execute a treatment protocol when the energy application device 206 is positioned at a selected treatment position.

The system may also include an imaging device that facilitates focusing the energy application device 206. In one embodiment, the imaging device may be integrated with or the same device as the energy application device 206 such that different ultrasound parameters (frequency, aperture, or energy) are applied for selecting (e.g., spatially selecting) a region of interest and for focusing energy to the selected region of interest for targeting and subsequently neuromodulation. In another embodiment, the memory 232 stores one or more targeting or focusing modes that is used to spatially select the region of interest within an organ or tissue structure. Spatial selection may include selecting a subregion of an organ to identify a volume of the organ that corresponds to a region of interest. Spatial selection may rely on image data as provided herein. Based on the spatial selection, the energy application device 206 may be focused (e.g., using the beam controller 237) to a focus location on the selected volume corresponding to the region of interest. It should be understood that the image data used to guide the focus location may be a volume or a plane. For example, the energy application device 206 may be configured to first operate in the validating mode to acquire the selected treatment position by capturing image data to be used for identifying the selected treatment position associated with capturing the region of interest. The validating mode energy is not at levels and/or applied with modulation parameters suitable for neuromodulating treatment. However, once the region of interest is identified, the controller 216 may then operate in a treatment mode according to the modulation parameters associated with achieving targeted physiological outcomes.

The target tissue may be an internal tissue or an organ that includes synapses of axon terminals and non-neuronal cells. The synapses may be stimulated by direct application of ultrasound energy to the axon terminals within a field of focus of the ultrasound transducer focused on a region of interest 20 of the target tissue to cause release of molecules into the synaptic space. The region of interest may be selected to include a certain type of axon terminal, such as an axon terminal of a particular neuron type and/or one that forms a synapse with a certain type of non-neuronal cell. Accordingly, the region of interest 20 may be selected to correspond to a portion of the target tissue with the desired axon terminals (and associated non-neuronal cells). The energy application may be selected to preferentially trigger a release of one or more molecules such as neurotransmitters from the nerve within the synapse or directly activate the non-neuronal cell itself through direct energy transduction, or cause an activation within both the neural and non-neuronal cells that elicits a desired physiological effect.

The controller 216 may also be configured to receive inputs related to the targeted physiological outcomes as an input to the selection of the modulation parameters. For example, when an imaging modality is used to assess tissue displacement, the controller 216 may be configured to receive a calculated index or parameter of the characteristic (e.g., a total displacement, a rate of change of displacement). Based on whether the index or parameter is above or below a predefined threshold, an indication of the diagnosis or related to therapy goals being reached may be provided (e.g., via a display). In one embodiment, the parameter may be a measure of tissue displacement of the affected tissue or a measure of depth of the affected tissue. Other parameters may include assessing a concentration of one or more molecules of interest (e.g., assessing one or more of a change in concentration relative to a threshold or a baseline/control, a rate of change, determining whether concentration is within a desired range). Further, the energy application device 206 (e.g., an ultrasound transducer) may operate under control of the controller 216 to a) acquire image data of a tissue that may be used to spatially select a region of interest within the target tissue b) apply the modulating energy to the region of interest and c) acquire image data to determine that the targeted physiological outcome has occurred (e.g., via displacement measurement). In such an embodiment, the imaging device, the assessment device 220 and the energy application device 206 may be the same device.

In an embodiment, the system 200 may be configured to set control parameters for the therapy transducer 208 to achieve a particular profile, changes in a molecule of interest, or characteristic tissue displacement. For example, subject responses to neuromodulating energy may vary, and different control parameters may be involved to achieve similar displacement between subjects. The control parameters may be tuned until a characteristic tissue displacement is achieved. The characteristic or target tissue displacement may be a total displacement metric or may be a threshold or range based on the metric, whereby achieving displacement values within a target range is indicative of successful treatment. In an embodiment, the characteristic tissue displacement is a presence of two thresholds, a low threshold and a high threshold, and a target range is displacement that is between the two thresholds. The control parameters associated with the thresholds may vary from subject to subject, and the system 200 may be tuned to identify the thresholds based on a trial or calibrating protocol applied to the subjects. Once identified for each subject, the associated parameters that achieve displacement between the thresholds and in the effective therapy range may be used over the course of the therapy protocol. The tissue displacement, or lack of achieving a characteristic or target displacement, may also be used to select a new region of interest 202. In one example, a region of interest 202 may be less therapeutically effective over time. This decrease in therapeutic effectiveness may be identified by changes or decrease in tissue displacement over the course of a therapy protocol. In another example, more responsive regions of interest 202 may be identified or mapped based on tissue displacement. In one embodiment, at an initiation of therapy, the target tissue 200 may be mapped using desired control parameters to identify subregions of an organ or tissue that are more responsive based on a degree of tissue displacement caused by applying ultrasound energy at the control parameters. Once mapped, the region of interest 202 may be selected from top-ranked regions in responsiveness (i.e., tissue displacement) that are also physically located in regions that contain one or more axon terminals that, when stimulated, cause a desired physiological response. This may vary from subject-to-subject as well as within a subject over time.

The neuromodulation techniques discussed herein may be used to cause a change in concentration (e.g., increased, decreased) of a molecule of interest and/or a change in characteristics of a molecule of interest. That is, the treatment may cause changes in tissue production or release of one or more molecules of interest (e.g., a first molecule of interest, a second molecule of interest, and so on) and may refer to changing a concentration (circulating, tissue) or characteristics (covalent modification) of a molecule as a result of energy application to one or more regions of interest (e.g., a first region of interest, a second region of interest, and so on) in one or more tissues (e.g., a first tissue, a second tissue, and so on). Changes in a molecule of interest may include changes in characteristics of the molecule such as expression, secretion, translocation of proteins and direct activity changes. The changes may be driven based on the effect of the applied energy on ion channels, either driving nerve activity and function itself or modulation of neighboring non-neuronal cells as a result of molecules derived from the neural activity or direct activation within the non-neuronal cell. Changes in a molecule of interest may also refer to maintaining a desired concentration of the molecule, such that expected changes or fluctuations in concentration (e.g., as a result of eating) do not occur as a result of the neuromodulation. Changes in a molecule of interest may refer to causing changes in molecule characteristics, such as enzyme-mediated covalent modification (changes in phosphorylation, aceylation, ribosylation, etc.). That is, it should be understood that changes in a molecule of interest may refer to molecule concentration and/or molecule characteristics. The molecule of interest may be a biological molecule, such as one or more of carbohydrates (monosaccharaides, polysaccharides), lipids, nucleic acids (DNA, RNA), or proteins. In certain embodiments, the molecule of interest may be a signaling molecule such as a hormone (an amine hormone, a peptide hormone, or a steroid hormone).

Figure 19:
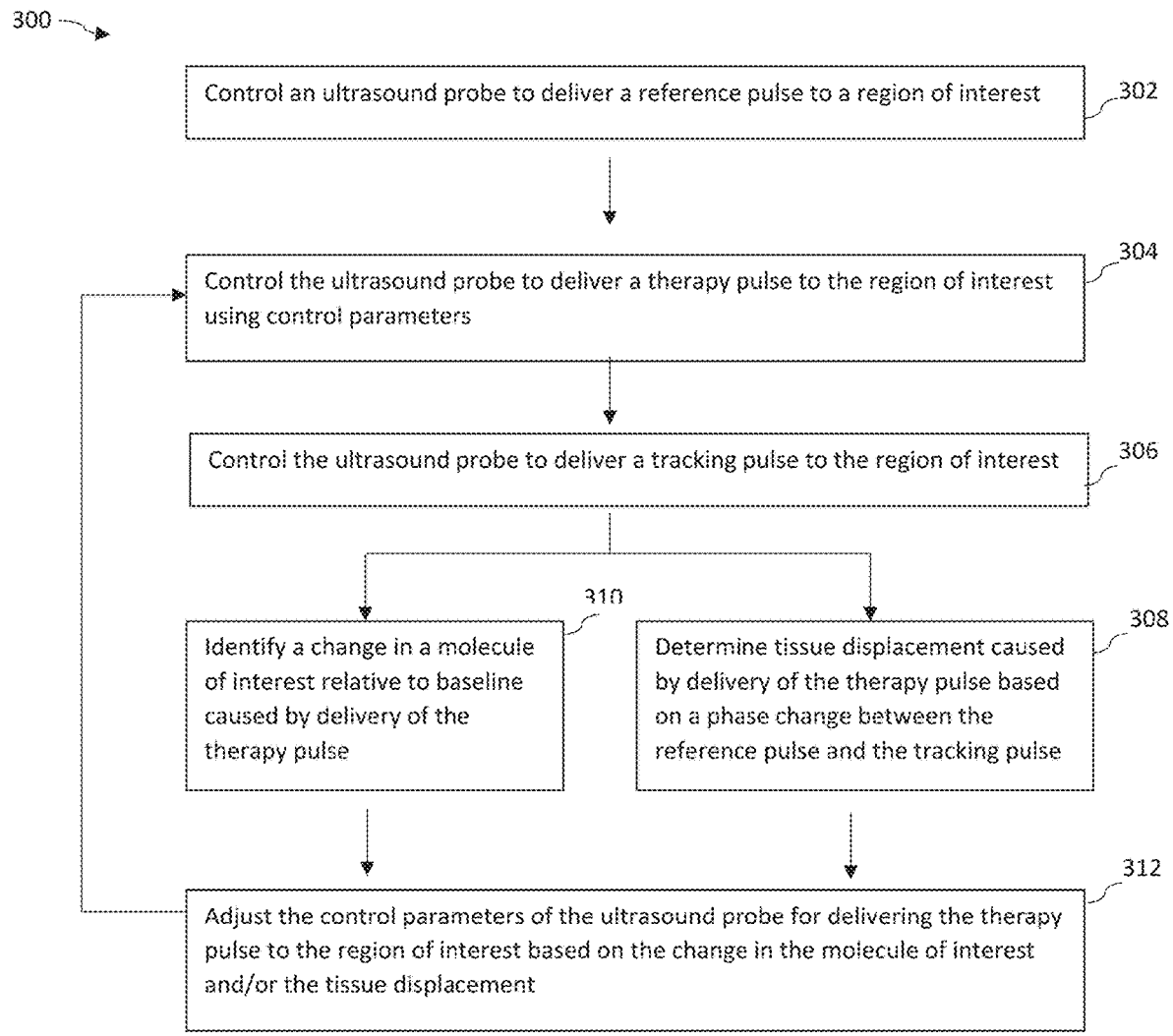
FIG. 19 is a flow diagram of a technique for tuning tissue displacement according to embodiments of the disclosure.

Physiological differences between subjects may yield variability in levels of tissue displacement associated with achieving a target increase or decrease in concentration of the molecule of interest, or other type of change in the molecule of interest (e.g., a change in activation status of the molecule). FIG. 19 is a flow diagram of a method 300 for tuning control parameters of a therapy pulse to achieve one or both of a desired tissue displacement and/or a characteristic or threshold change in a molecule of interest relative to baseline measurement acquired at or before initiation of treatment. In the method 300, a transducer of an ultrasound probe delivers a reference imaging pulse to the region of interest and collects reflected ultrasound waves from the tissue to generate baseline or reference data (block 302), which is received by a controller of the ultrasound probe (e.g., an ultrasound system). A same ultrasound transducer of the ultrasound probe or a different ultrasound transducer (e.g., a dedicated therapy transducer) is controlled to apply an ultrasound therapy pulse (block 304). A tracking pulse is delivered subsequent to applying the ultrasound energy (block 306), and the tissue displacement is determined based on a phase change between the reference pulse and the tracking pulse (block 308). In certain embodiments, changes in a molecule of interest are identified (block 310) and are used to assess the effectiveness of the therapy pulse. In certain embodiments, the tissue displacement is used to assess the effectiveness of the therapy pulse. Based on the change in the molecule of interest and/or the tissue displacement, the control parameters of the therapy pulse may be tuned (block 312) to calibrate the therapy pulse for the patient and to facilitate more effective neuromodulating treatment.

For example, one or more of the driving voltage, the pulse repetition interval, and the pulse length may be adjusted to adjust the control parameters of the therapy pulse. In one embodiment, a subject-specific calibration may be performed in which a control parameter of a therapy pulse is applied and cycled through various settings while g a concentration of the molecule of interest is tracked at the various settings. An effective range of the parameter is identified in which the desired effect (e.g., a threshold % change from baseline) is observed. For example, as shown in FIG. 7, increasing a cycle number of a 200 ms pulse identified a range of cycles (150-250 cycles) for which the therapy pulse caused a significant percentage change in glucose concentration relative to baseline. Future therapy pulses may be applied using a setting of the control parameter within the range associated with the observed desired change in the molecule of interest. In another embodiment, the tissue displacement may be tracked during adjustment of the control parameter. Future therapy pulses may be applied to cause the tissue displacement that is associated with the observed desired change in the molecule of interest during calibration (e.g., a particular displacement at a particular percentage change in the molecule of interest relative to baseline). This may result in dynamic adjustment of the control parameters to different settings for different doses as the subject's tissue may respond differently over the course of the treatment protocol based on the subject's metabolic state or clinical condition. It should be understood that the adjustment of the control parameters may be adjustment of one or more control parameters and may include combinations of control parameters associated with desired physiological outcomes. Further, the adjustment may be an adjustment to an Isppa or Ispta of the therapy pulse. In an embodiment, the adjustment may include distributing the therapy pulse between multiple regions of interest or consolidating a distributed dose to a single region of interest based on an assessment of the change in the molecule of interest. For example, a treatment protocol may initiate with application of the dose to a single region of interest. Over time, compensation or other effects may decrease the effectiveness of the therapy pulse using the initial control parameters. The treatment protocol may include certain doses that are distributed between multiple sites to avoid such compensation.

The change in the molecule of interest may be a deviation from a threshold concentration or a concentration outside of a particular range. The change in the molecule of interest may be a percentage change from baseline, which may be above or below a threshold percentage change. For example, a treatment protocol may have a threshold therapy goal of causing a molecule of interest to change in concentration (increase or decrease) at least 50%. If the therapy goal threshold is not reached, the control parameters are adjusted until the threshold associated with the therapy goal is reached and the method 300 may iterate back to block 304 until the threshold is exceeded. In an embodiment, the threshold may be an increase in concentration of the molecule of interest of at least 100%. In an embodiment, the therapy goal may be achieving a concentration of the molecule of interest within a particular range.

Technical effects of the present disclosure include controlled application of neuromodulating energy (e.g., ultrasound energy) to cause tissue displacement that is associated with a desired physiological outcome. By tracking tissue displacement as a marker of therapy effectiveness, neuromodulation delivery systems may operate more efficiently by achieving desired displacement at lower overall energy levels. Further, the neuromodulating energy may be delivered within a zone of therapeutic effectiveness correlated with a target tissue displacement that avoids lower applied energies that are not effective as well as higher applied energies that may be associated with heat and/or cavitation effects in the tissue.

This written description uses examples, including the best mode, and also to enable any person skilled in the art to practice the disclosed techniques including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A neuromodulation delivery system, comprising:
an energy application device configured to deliver energy to an internal tissue in a subject; and
a controller configured to:
control application of the energy via the energy application device to a plurality of locations of the internal tissue to deliver the energy thereto, wherein the energy application device is controlled under first control parameters;
receive image data of the plurality of locations during the application of the energy;
track real-time tissue displacement of the plurality of locations of the internal tissue using the image data;
rank individual locations of the plurality of locations based on the real-time tissue displacement, wherein the individual locations control glucose concentration in the blood;
identify one or more top-ranked individual locations based on the ranking; and
control the energy application device to apply a neuromodulating energy dose using second control parameters to the identified one or more top-ranked individual locations to effect therapeutic changes in blood glucose concentrations.

2. The system of claim 1, wherein the energy application device comprises an ultrasound therapy transducer.

3. The system of claim 2, wherein the energy application device comprises an imaging transducer configured to acquire the image data.

4. The system of claim 1, wherein the controller is configured to acquire a baseline image of the internal tissue and determine the tissue displacement based on the baseline image and the image data.

5. The system of claim 1, wherein the controller is configured to generate a responsiveness map of the internal tissue based on the real-time tissue displacement.

6. The system of claim 1, wherein the control parameters comprise one or more of driving voltage, pulse length, pulse duration, and pulse repetition interval.

7. The system of claim 6, wherein the first control parameters are the same as the second control parameters.

8. The system of claim 6, wherein the first control parameters are the same between the plurality of locations.

9. The system of claim 1, wherein the internal tissue is an organ.

10. The system of claim 1, wherein the controller is configured to control the application of the energy via the energy application device to the plurality of locations of the internal tissue at an initiation of therapy.

11. A neuromodulation delivery system, comprising:
an ultrasound probe configured to deliver neuromodulating energy to an internal tissue in a subject via a therapy transducer and acquire image data of the internal tissue via an imaging transducer; and
a controller configured to:
set a characteristic tissue displacement between a first threshold displacement and a second threshold displacement;
control application of the neuromodulating energy via the therapy transducer of the ultrasound probe to a location of the internal tissue to deliver the neuromodulating energy thereto, wherein the therapy transducer is controlled under control parameters;
receive the image data of the location acquired by the imaging transducer of the ultrasound probe during the application of the neuromodulating energy;
track real-time tissue displacement of the location during the application of the neuromodulating energy based on the image data; and
tracking a change in glucose concentration based on the tracked real-time tissue displacement.

12. The system of claim 11, wherein the controller is configured to:
receive additional image data of the location acquired by the imaging transducer of the ultrasound probe during the application of additional neuromodulating energy using modified control parameters;
track second real-time tissue displacement of the location during the application of the additional neuromodulating energy based on the image data;
determine that the second real-time tissue displacement is the characteristic tissue displacement; and
set the location as a region of interest for the modified control parameters.

13. The system of claim 12, wherein the controller is configured to:
modify subsequent control parameters for doses of a therapy protocol applied to the location such that subsequent tracked tissue displacement at the location is a set tissue displacement.

14. The system of claim 11, wherein the controller is configured to:
receive additional image data of a second location acquired by the imaging transducer of the ultrasound probe during the application of additional neuromodulating energy using the control parameters;
track second real-time tissue displacement of the second location during the application of the additional neuromodulating energy based on the image data;
determine that the second real-time tissue displacement is the characteristic tissue displacement; and
set the second location as a region of interest for the control parameters.

15. The system of claim 11, wherein the control parameters comprise one or more of driving voltage, pulse length, pulse duration, and pulse repetition interval.

16. The system of claim 11, wherein the internal tissue is an organ.

17. A method of delivery of neuromodulating energy, the method comprising:

setting a characteristic tissue displacement for a region of interest in an internal tissue of a subject between a first threshold displacement and a second threshold displacement;

delivering a reference pulse to the region of interest via an energy application device;

delivering a therapy pulse to the region of interest via the energy application device subsequent to delivering the reference pulse, wherein the therapy pulse is delivered using control parameters of the energy application device;

delivering a tracking pulse to the region of interest via the energy application device subsequent to delivering the therapy pulse;

identifying a phase change between the reference pulse and the tracking pulse;

determining a tissue displacement in or near the region of interest based on the phase change;

determining that the tissue displacement deviates from the set characteristic tissue displacement, wherein the reference and tracking pulse do not cause displacement and the tissue displacement is in response to the therapy pulse; and adjusting the control parameters of the therapy pulse based on the determined tissue displacement.

18. The method of claim 17, wherein the reference pulse and the tracking pulse are delivered by an imaging transducer and the therapy pulse is delivered by a therapy transducer.

19. The method of claim 17, wherein the tissue displacement is determined based on an area under a curve of the identified phase change.

20. The method of claim 17, comprising applying a neuromodulating energy dose via the energy application device to the region of interest using the adjusted control parameters.

* * * * *